United States Patent
Oh et al.

(10) Patent No.: US 10,765,655 B2
(45) Date of Patent: Sep. 8, 2020

(54) COMPOSITION CONTAINING MONOACETYLDIGLYCERIDE COMPOUND AS ACTIVE INGREDIENT FOR PREVENTING OR TREATING CHRONIC OBSTRUCTIVE PULMONARY DISEASE

(71) Applicants: ENZYCHEM LIFESCIENCES CORPORATION, Daejeon (KR); KOREA RESEARCH INSTITUTE OF BIO SCIENCE AND BIOTECHNOLOGY, Daejeon (KR)

(72) Inventors: Sei-Ryang Oh, Daejeon (KR); Kyung Seop Ahn, Daejeon (KR); Su Ui Lee, Daejeon (KR); In Sik Shin, Daejeon (KR); Ok-Kyoung Kwon, Daejeon (KR); Seung Hyung Kim, Daejeon (KR); Chan Mi Chun, Daejeon (KR); Tae-Suk Lee, Daejeon (KR); Yong-Hae Han, Seoul (KR); Ki Young Sohn, Seoul (KR); JongKoo Kang, Chungcheongbuk-do (KR); Hye Kyung Kim, Seoul (KR)

(73) Assignees: Enzychem Lifesciences Corporation, Daejeon (KR); Korea Research Institute of BioScience and Biotechnology, Daejeon (KR)

( * ) Notice: Subject to any disclaimer, the term of this patent is extended or adjusted under 35 U.S.C. 154(b) by 0 days.

(21) Appl. No.: 15/857,933

(22) Filed: Dec. 29, 2017

(65) Prior Publication Data

US 2018/0280336 A1 Oct. 4, 2018

Related U.S. Application Data

(62) Division of application No. 14/912,765, filed as application No. PCT/KR2014/007661 on Aug. 19, 2014, now abandoned.

(30) Foreign Application Priority Data

Aug. 19, 2013 (KR) .......................... 10-2013-0098184

(51) Int. Cl.
 *A61K 31/231* (2006.01)
(52) U.S. Cl.
 CPC .................. *A61K 31/231* (2013.01)
(58) Field of Classification Search
 None
 See application file for complete search history.

(56) References Cited

U.S. PATENT DOCUMENTS

2010/0010087 A1 1/2010 Hong

FOREIGN PATENT DOCUMENTS

| JP | 2004-18519 A | 1/2004 |
| KR | 10-2000-0071887 A | 11/2000 |
| KR | 10-2005-0103259 A | 10/2005 |
| KR | 10-2006-0047447 A | 5/2006 |
| WO | 199926640 A1 | 6/1999 |

OTHER PUBLICATIONS

Kou et al (Evidence Based Complementary and Alternative Medicine, 2012:1-10, 2012) (Year: 2012).*
Barnes (J Clinical Investigation 118:3546-3556, 2008) (Year: 2008).*
Barnes (Am J Respir Cell Mol Biol 41:631-638, 2009—identified as Barnes II) (Year: 2009).*
Shin, In-Sik, et al., "EC-18, a synthetic monoacetyldiglyceride (1-palmitoyl-2-linoleoyl-3-acetylglycerol), attenuates the asthmatic response in aluminum hydroxide/ovalburmin-induced model of asthma", International Immunopharmacology, vol. 18, pp. 116-123, 2014.
International Preliminary Report on Patenability issued in corresponding International application No. PCT/KR2014/007661.

* cited by examiner

*Primary Examiner* — Craig D Ricci
(74) *Attorney, Agent, or Firm* — Mintz Levin Cohn Ferris Glovsky and Popeo, P.C.; Peter F. Corless

(57) ABSTRACT

The present invention relates to a pharmaceutical composition containing a monoacetyldiacylglycerol compound as an active ingredient for preventing or treating chronic obstructive pulmonary diseases, and a functional health food composition for treating or preventing chronic obstructive pulmonary diseases. The monoacetyldiacylglycerol compound of the present invention inhibits the IL-4 expression in EL-4 cells and inhibits the infiltration of inflammatory cells into the bronchial tube in an animal model. In addition, the compounds of the present invention have an excellent effect of inhibiting the expression of CXCL-1, TNF-α, or MIP-2, thereby overcoming side effects of the currently used therapeutic agents for chronic obstructive pulmonary diseases, having no toxicity, and exhibiting a superior therapeutic effect, and thus can be useful as a composition for preventing, treating, and alleviating chronic obstructive pulmonary diseases.

5 Claims, No Drawings
Specification includes a Sequence Listing.

SEQUENCE LISTING

```
<160> NUMBER OF SEQ ID NOS: 4

<210> SEQ ID NO 1
<211> LENGTH: 21
<212> TYPE: DNA
<213> ORGANISM: artificial sequence
<220> FEATURE:
<223> OTHER INFORMATION: IL-4 sense primer

<400> SEQUENCE: 1
gaatgtacca ggagccatat c                                              21

<210> SEQ ID NO 2
<211> LENGTH: 21
<212> TYPE: DNA
<213> ORGANISM: Artificial Sequence
<220> FEATURE:
<223> OTHER INFORMATION: IL-4 antisense primer

<400> SEQUENCE: 2
ctcagtacta cgagtaatcc a                                              21

<210> SEQ ID NO 3
<211> LENGTH: 20
<212> TYPE: DNA
<213> ORGANISM: Artificial Sequence
<220> FEATURE:
<223> OTHER INFORMATION: GAPDH sense primer

<400> SEQUENCE: 3
aactttggca ttgtggaagg                                                20

<210> SEQ ID NO 4
<211> LENGTH: 20
<212> TYPE: DNA
<213> ORGANISM: Artificial Sequence
<220> FEATURE:
<223> OTHER INFORMATION: GAPDH antisense primer

<400> SEQUENCE: 4
acacattggg ggtaggaaca                                                20
```

COMPOSITION CONTAINING MONOACETYLDIGLYCERIDE COMPOUND AS ACTIVE INGREDIENT FOR PREVENTING OR TREATING CHRONIC OBSTRUCTIVE PULMONARY DISEASE

This is a Divisional Application of U.S. patent application Ser. No. 14/912,765, filed Feb. 18, 2016, an application filed as a national stage under 371 of Application No. PCT/KR2014/007661 filed Aug. 19, 2014, and claiming benefit from Korean Application No. 1020130098184, filed Aug. 19, 2013, the content of each of which is hereby incorporated by reference in its entirety.

TECHNICAL FIELD

The present invention relates to a pharmaceutical composition for preventing or treating chronic obstructive pulmonary disease, and a functional health food for preventing or alleviating chronic obstructive pulmonary disease, which contain, as an active ingredient, a monoacetyldiacylglycerol compound or a pharmaceutically acceptable salt thereof.

The Sequence Listing submitted in text format (.txt) filed on Dec. 29, 2017, named "po10498us_ST25.txt", (created on Oct. 29, 2016, 7 MB), is incorporated herein by reference.

BACKGROUND ART

Chronic obstructive pulmonary disease (COPD) is a lung disease that causes narrowing of the airways due to an abnormal inflammatory response in the lung. It is known that chronic obstructive pulmonary disease is caused mainly by inhalation of noxious particles or gases, and particularly, smoking is the major cause of chronic obstructive pulmonary disease. Currently, the prevalence of chronic obstructive pulmonary disease among people aged over 40 years in Korea is increasing every year. In addition, chronic obstructive pulmonary disease is the only disease with increasing incidence and prevalence worldwide, and is anticipated to become the third leading cause of death in 2020 worldwide. Smoking acts as a potent stimulus in lung tissue to increase the production of various proinflammatory factors, growth factors, oxidants and chemotactic factors and activate inflammatory signaling systems to thereby stimulate the migration of numerous inflammatory cells, including neutrophils and macrophages, thereby making lung inflammation worse. Proteases such as metalloproteinase derived from cigarette smoke and inflammatory cells are activated to destroy structures in interstitial tissue. This results in abnormal changes in lung tissue, for example, airway wall thickening and pulmonary fibrosis, which deteriorate lung function. Thus, various agents for the prevention and treatment of chronic obstructive pulmonary disease have been developed with a focus on alleviation of lung inflammation that is the major cause of the disease. Among them, treatment with steroidal agents and antibiotics for alleviation of inflammation in chronic obstructive pulmonary disease can be a very attractive treatment method, similar to asthma treatment. However, steroidal agents and antibiotics have limitations in that they can cause many side effects due to immune suppression and tolerance, and thus are not suitable for chronic obstructive pulmonary disease patients in need of long-term treatment.

EC-18, as a kind of monoacetyldiglyceride compounds, was separated or extracted from the natural deer antler. EC-18 is known to be hematopoiesis. Also, it is known that EC-18 increases survivability ratio of animals in sepsis animal model experiment using cecal-ligation-puncture, and shows no-toxicity in GLP (Good Laboratory Practice) toxicity test. However, the effect of monoacetyldiacylglycerol compounds including EC-18 is not known or disclosed in chronic obstructive pulmonary disease. Accordingly, the present inventors have made extensive efforts to develop an agent for treating chronic obstructive pulmonary disease, which is derived from a natural material or is a new compound. As a result, the present inventors have found that a monoacetyldiacylglycerol compound inhibits secretion of CXCL-1, TNF-α or MIP-2 and inhibits infiltration of inflammatory cells into bronchi, and thus can be effectively used for the prevention or treatment of chronic obstructive pulmonary disease, thereby completing the present invention.

DISCLOSURE

Technical Problem

It is an object of the present invention to provide a pharmaceutical composition for preventing or treating chronic obstructive pulmonary disease, and a functional health food for preventing or alleviating chronic obstructive pulmonary disease, which contain, as an active ingredient, a monoacetyldiacylglycerol compound represented by the following formula 1.

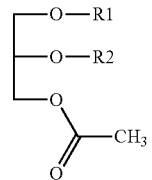

[Formula 1]

wherein R1 and R2 are independently a fatty acid residue of 14 to 22 carbon atoms.

Another object of the present invention is to provide a method for preventing or treating chronic obstructive pulmonary disease, which comprises administering the pharmaceutical composition to a subject who is at risk of developing chronic obstructive pulmonary disease or suffers from chronic obstructive pulmonary disease.

Technical Solution

To achieve the above objects, in one aspect, the present invention provides a pharmaceutical composition for preventing or treating chronic obstructive pulmonary disease, which contain, as an active ingredient, a monoacetyldiacylglycerol compound represented by the following formula 1 or a pharmaceutically acceptable salt thereof:

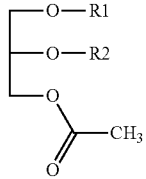

[Formula 1]

wherein R1 and R2 are independently a fatty acid group of 14 to 22 carbon atoms. In the Specification, the fatty acid group means the carboxyl group of fatty acids from which —OH group is extracted.

In detail, the pharmaceutical composition for preventing or treating asthma according to the present invention includes a monoacetyldiacylglycerol compound represented by the Formula 1. In the present invention, the term "monoacetyl diacyl glycerol compound" means glycerol compounds having one acetyl group and two acyl groups, and can be referred as "monoacetyl diacyl glycerol (MADG)".

In the monoacetyl diacyl glycerol compound of Formula 1, R1 and R2 are independently a fatty acid residue of 14 to 22 carbon atoms. Preferably, non-limiting examples of R1 and R2 include palmitoyl, oleoyl, linoleoyl, linolenoyl, stearoyl, myristoyl, arachidonoyl, and so on. Preferable combinations of R1 and R2 (R1/R2) include oleoyl/palmitoyl, palmitoyl/oleoyl, palmitoyl/linoleoyl, palmitoyl/linolenoyl, palmitoyl/arachidonoyl, palmitoyl/stearoyl, palmitoyl/palmitoyl, oleoyl/stearoyl, linoleoyl/palmitoyl, linoleoyl/stearoyl, stearoyl/linoleoyl, stearoyl/oleoyl, myristoyl/linoleoyl, myristoyl/oleoyl, and so on. In optical activity, the monoacetyl diacyl glycerol compound of Formula 1 can be (R)-form, (S)-form or a racemic mixture.

In one embodiment, the monoacetyl diacyl glycerol compound is a compound of the following Formula 2.

[Formula 2]

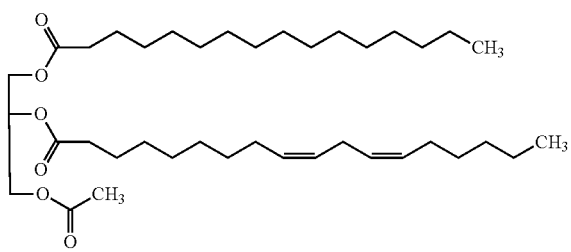

The compound of Formula 2 is 1-palmitoyl-2-linoleoyl-3-acetylglycerol, sometimes referred as "EC-18" in this specification. R1 and R2 of the compound of Formula 2 are palmitoyl and linoleoyl, respectively.

The monoacetyldiacylglycerol compound may be extracted/isolated from deer antler or prepared by a known organic synthesis method (Korean Patent No. 10-0789323). Specifically, a chloroform extract of deer antler can be prepared by extracting deer antler with hexane, further extracting the extraction residue with chloroform, and then distilling the resulting extract under reduced pressure. The amount of each of hexane and chloroform that are used as the extraction solvents in the extraction process is used in an amount enough to submerge the deer antler. Generally, each of hexane and chloroform may be used in an amount of about 4-5 liters per kg of the deer antler, but the kinds and amounts of extraction solvents used are not limited thereto. The chloroform extract of deer antler obtained by the above-described method may subsequently be fractionated and purified by a series of silica gel chromatography and TLC methods, thereby obtaining the monoacetyldiacylglycerol compound that is used in the present invention. As an eluent in the chromatographic purification step, chloroform/methanol, hexane/ethyl acetate, hexane/ethyl acetate/acetic acid, or the like, may be used, but is not limited thereto.

Meanwhile, a method for chemically synthesizing the monoacetyldiacylglycerol compound that is used in the present invention is disclosed in Korean Patent No. 10-0789323. Specifically, the method for synthesizing the desired monoacetyldiacylglycerol compound may comprise the processes of: (a) attaching a protecting group to position 3 of 1-R1-glycerol to prepare 1-R1-3-protecting group-glycerol; (b) introducing an R2 group into position 2 of 1-R1-3-protecting group-glycerol to prepare 1-R1-2-R2-3-protecting group-glycerol; and (c) performing simultaneous deprotection and acetylation of 1-R1-2-R2-3-protecting-glycerol. The acetylated compound may, if necessary, be purified. In another method, the monoacetyldiacylglycerol compound can also be obtained by acetolysis of phosphatidylcholine, but is not limited thereto. All stereoisomers of the compound of formula 1 may fall within the scope of the present invention.

It has been found in the present invention that the monoacetyldiacylglycerol compound can reduce secretion of IL-4, CXCL-1, TNF-α or MIP-2, indicating that it can be effectively used for the prevention or treatment of chronic obstructive pulmonary disease. As used herein, the term "chronic obstructive pulmonary disease" refers to a respiratory disease in which an abnormal inflammatory response in the lung is caused by the inhalation of noxious particles or gases, and for this reason, the obstruction of airflow progresses to deteriorate lung function and cause difficulty in breathing. Main symptoms of chronic obstructive pulmonary disease include breathlessness, chronic cough and chronic sputum production, and bronchodilators, such as beta-agonists, anticholinergics or methylxanthine drugs, or inhaled corticosteroids, are typically used as agents for treating chronic obstructive pulmonary disease. In the present invention, the chronic obstructive pulmonary disease may preferably be chronic bronchitis or emphysema, but is not limited thereto. As used herein, the term "chronic bronchitis" refers to a disease which continues for two or more years and in which cough with sputum production continues for three months per year. Chronic bronchitis is believed to be caused by bronchial injury resulting from stimuli such as smoking, air pollution, occupational exposure and the like, and main symptoms thereof include chronic cough, sputum production, and difficulty in breathing in exercise. In addition, acute exacerbation that is the feature of chronic obstructive pulmonary disease may appear, and at the same time, difficulty in breathing is quickly exacerbated for a period ranging from few hours to few days, and the amount of sputum increases or sputum changes from mucoid to purulent while having a dark yellow or bluish color, and becomes thick and hard to cough up. As used herein, the term "emphysema" refers to the abnormal permanent enlargement and destruction of the airspaces distal to the terminal bronchioles with the destruction of the alveoli. It is known that emphysema is caused by the inhalation of noxious particles and gases and that the most clinically significantly risk factor of emphysema is smoking. Main symptoms of emphysema include chronic cough and sputum production, difficulty in breathing, etc. As used herein, the term "preventing" refers to all actions that inhibit or delay the development of chronic obstructive pulmonary disease by administering the composition, and the term "treating" refers to all actions that alleviate or beneficially chronic obstructive pulmonary disease symptoms by administering the composition.

Cytokines such as IL-4 are closely associated not only with bronchial inflammation, but also with airway hyperresponsiveness, and airway hyperresponsiveness is the major risk factor of chronic obstructive pulmonary disease (Chest 2004, 126(6), 1832-9). Thus, the inhibition of expression of IL-4 can inhibit bronchial inflammation and reduce airway hyperresponsiveness to thereby inhibit the progression of chronic obstructive pulmonary disease. It is known that cytokines such as TNF-α and CXC chemokines such as MIP-2 are involved in the trafficking of neutrophils from the pulmonary circulation to the alveoli. These are all inflammation-associated cytokines or chemokines, and in the case of chronic obstructive pulmonary disease, the number of neutrophils increases and these cytokines or chemokines are secreted. Thus, inflammation occurs in the airways, the muscular wall thickens, and mucus secretion increases, resulting in bronchial obstruction. When the bronchus is obstructed, the alveoli are enlarged so that the ability to exchange oxygen and carbon dioxide will be impaired and the occurrence of respiratory failure will increase. In particular, it was found that the expression of these cytokines and chemokines in patients suffering from chronic obstructive pulmonary disease (COPD) increases, indicating that these cytokines and chemokines are associated with chronic obstructive pulmonary disease. Thus, the symptoms of chronic obstructive pulmonary disease can be inhibited by inhibiting the secretion of a protein selected from the group consisting of IL-4, CXCL-1, TNF-α and MIP-2.

In examples of the present invention, i) the inhibitory activities of monoacetyldiacylglycerol compounds against phorbol myristate acetate (PMA)-induced IL-4 expression in EL-4 cells that are mouse T cell lymphoma cells were measured, and as a result, it was found that a number of monoacetyldiacylglycerol compounds, including EC-18, showed significant inhibitory activities (Example 2), and ii) the expression levels of CXCL-1, TNF-α and MIP-2 in the bronchoalveolar lavage fluids from asthma-induced animal models were measured, and as a result, the expression levels of CXCL-1, TNF-α and MIP-2 in the COPD-induced group all greatly increased compared to those in the normal control group, whereas the expressions of these factors in the group administered with the monoacetyldiacylglycerol compound (EC-18) significantly decreased (Example 6). This suggests that the monoacetyldiacylglycerol compound is effective for the treatment of chronic obstructive pulmonary disease.

In addition, it has been found in the present invention that the monoacetyldiacylglycerol compound can reduce the number of inflammatory cells around the bronchus or can reduce the number of CD4$^+$ cells and neutrophils (Gr-1$^+$ cells). CD4$^+$ cells are known as cells that enhance immunity, and when the CD4$^+$ cells excessively increase, autoimmunity can occur. It is known that the number of CD4$^+$ cells in chronic obstructive pulmonary disease patients increases compared to that in normal people (Proceedings of the American Thoracic Society, Vol. 4, No. 7 (2007), pp. 512-521.). Meanwhile, the number of neutrophils (Gr-1$^+$ cells) in chronic obstructive pulmonary disease also increases (Eur Respir J 2011; 38: 285-294; Nikota et al. Respiratory Research 2011, 12:39). Thus, the symptoms of chronic obstructive pulmonary disease can be inhibited by reducing the number of CD4$^+$ cells and neutrophils (Gr-1$^+$ cells).

In examples of the present invention, inflammatory cells in lung tissue were measured by trypan blue staining, and CD4$^+$ cells and neutrophils (Gr-1$^+$ cells) were observed by immunofluorescence staining and flow cytometry. As a result, i) it was observed that the number of inflammatory cells in the COPD-induced group significantly increased, whereas the number of inflammatory cells in all the groups administered with the monoacetyldiacylglycerol compounds (EC-18) decreased (Example 4), and ii) It was observed that the number of CD4$^+$ cells and neutrophils (Gr-1$^+$ cells) in the COPD-induced group increased, whereas the number of CD4$^+$ cells and neutrophils (Gr-1$^+$ cells) in all the groups administered with the monoacetyldiacylglycerol compounds (EC-18) significantly decreased (Example 5). Such results also suggest that the monoacetyldiacylglycerol compounds are effective for the treatment of chronic obstructive pulmonary disease.

The pharmaceutical composition containing monoacetyldiacylglycerol compounds of the present invention may additionally include conventional pharmaceutically acceptable carriers, excipients, or diluents. The amount of monoacetyldiacylglycerol compounds in the pharmaceutical composition can be widely varied without specific limitation, and is specifically 0.0001 to 100.0 weight %, preferably 0.001 to 50 weight %, more preferably 0.01 to 20 weight % with respect to the total amount of the composition.

The pharmaceutical composition may be formulated into various forms for oral or non-oral administration, for example one selected from a group consisting of tablet, bolus, powder, granule, capsule such as hard or soft gelatin capsule, emulsion, suspension, syrup, emulsifiable concentrate, sterilized aqueous solution, non-aqueous solution, freeze-dried formulation, suppository, and so on. In formulating the composition, conventional excipients or diluents such as filler, bulking agent, binder, wetting agent, disintegrating agent, and surfactant can be used. The solid formulation for oral administration includes tablet, bolus, powder, granule, capsule and so on, and the solid formulation can be prepared by mixing one or more of the active components and at least one excipient such as starch, calcium carbonate, sucrose, lactose, gelatin, and so on. Besides the excipient, a lubricant such as Magnesium stearate and talc can also be used. The liquid formulation for oral administration includes emulsion, suspension, syrup, and so on, and may include conventional diluents such as water and liquid paraffin or may include various such as wetting agent, sweeting agent, flavoring agent, and preserving agent. The formulation for non-oral administration includes sterilized aqueous solution, non-aqueous solution, freeze-dried formulation, suppository, and so on, and solvent for such solution may include propylene glycol, polyethylene glycol, vegetable oil such as olive oil, and ester for syringe injection such as ethyl oleate. Base materials of the suppository may include witepsol, macrogol, tween 61, cacao butter, Laurin and glycerogelatine.

The composition of the present invention can be administered in a pharmaceutically effective amount. The term "pharmaceutically effective amount" is used to refer to an amount which is sufficient to achieve a desired result in a medical treatment. The "pharmaceutically effective amount" can be determined in accordance with type, age and sex of a subject, severity and type of disease, activity of drug, sensitivity to drug, administration time, period and route, excretion rate, and other well known criteria in medical field. The composition of the present invention can be administered alone or with other medicines sequentially or simultaneously, or administered once or several times. Considering all the above factors, it is important to dose the amount that can achieve the maximum effect with the minimum amount with no side effects, which can be readily determined by those skilled in the art. The preferable amount of the composition of the present invention can be varied in accordance with the condition and weight of patient, severity of disease, formulation type of drug, administration route and period of drug. Appropriate total amount of administration per 1 day can be determined by a doctor of related medical filed, and generally 0.001 to 1000 mg/kg, preferably 0.05 to 200 mg/kg, more preferably 0.1 to 100 mg/kg once or several times by dividing in 1 day. The composition of the present invention can be administered to any subject which requires the suppression of blood cancer or cancer metastasis. For example, the composition of the present invention can be administered to not only human but also non-human animal (specifically mammals) such as monkey, dog, cat, rabbit, guinea pig, rat, mouse, cow, sheep, pig, goat, and so on. The composition of the present invention can be administered by conventional various methods, for example, by oral or rectum administration, or by intravenous, intramuscular, subcutaneous or cerebrovascular injection.

As other aspect of the present invention, the present invention provides a functional health food for preventing or alleviating chronic obstructive pulmonary disease, comprising monoacetyldiacylglycerol compounds of Formula 1 as an active component(s),

[Formula 1]

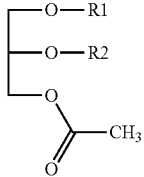

wherein R1 and R2 are independently a fatty acid group of 14 to 22 carbon atoms, but are not limited thereto.

In detail, the monoacetyldiacylglycerol compounds of the present invention can be included in the functional health food for preventing or alleviating chronic obstructive pulmonary disease. The monoacetyldiacylglycerol compounds, chronic obstructive pulmonary disease are previously explained in detail. The term "improving" means every change which reduces or advantageously changes the symptoms in a subject having or suspicious of having chronic obstructive pulmonary disease.

When the composition of the present invention is included in the health functional food, the composition can be included alone or with other active component. The amount of the compounds of the present invention in the health functional food can be determined in accordance with the intended use of the health functional food. Generally, when preparing health functional food or beverage, the composition of the present invention can be included in the amount of less than 15 weight part, preferably less than 10 weight part. In case of long term administration for maintaining one's health, the amount of the composition can be reduced. However, since the active component does not cause any adverse effect, the amount of the composition can be increased by more than the above mentioned amount. The health functional food including the composition of the present invention can be any conventional food or beverage. Specific examples of the food include meat, sausage, bread, chocolate, candy, snack, biscuit, pizza, Ramen, noodles, gum, ice cream, dairy product, soup, beverage, tea, drink, alcoholic drink, vitamin complex, and so on. If necessary, the food of the present invention can also include food for an animal.

When the health functional food is beverage, the beverage may include conventional sweetener, flavoring agent, natural carbohydrate, and so on. Examples of the natural carbohydrate include monosaccharide such as glucose and fructose, disaccharide such as maltose and sucrose, polysaccharide such as dextrin and cydodextrin, and sugar alcohol such as xylitol, sorbitol, and erythritol. The preferable amount of the natural carbohydrate can be about 0.01 to 0.04 g, more preferably about 0.02 to 0.03 g with respect to 100 m, of the beverage of the present invention. Examples of the sweetener includes natural sweeteners such as Thaumatin and *Stevia* extract and artificial sweeteners such as saccharin and aspartame. The health functional food of the present invention may further include various nutritional supplement, vitamin, electrolyte, flavoring agent, coloring agent, pectic acid and its salt, alginic acid and its salt, organic acid, protective colloid, thickener, pH adjuster, stabilizer, preservative, glycerin, alcohol, juice and so on.

As another aspect of the present invention, the present invention provides a method for preventing or treating chronic obstructive pulmonary disease, comprising a step of administering the pharmaceutical composition to a subject who is suspicious of having chronic obstructive pulmonary disease. The "subject who is suspicious of having chronic obstructive pulmonary disease" includes not only an animal including human being which has chronic obstructive pulmonary disease but also potentially has chronic obstructive pulmonary disease. The subject who is suspicious of having chronic obstructive pulmonary disease can be effectively treated by administering the pharmaceutical composition of the present invention. The term "administering" means introducing the pharmaceutical composition of the present invention into the subject who is suspicious of having chronic obstructive pulmonary disease by any means. The administration route can be any route such as oral or non-oral route.

A method for treating chronic obstructive pulmonary disease according to the present invention may comprise administering a pharmaceutically effective amount of a pharmaceutical composition comprising the monoacetyldiacylglycerol compound of formula 1 or a pharmaceutically acceptable salt thereof. The total amount per day of the compound or composition of the present invention can be determined by a physician within the range of reliable medical decisions. The compound of the present invention may be administered once or several times per day in an amount of generally 0.001-1000 mg/kg, preferably 0.05-200 mg/kg, more preferably 0.1-100 mg/kg. However, as for any specific patients, the specific therapeutically amount may vary depending on various factors, including the kind and degree of disease to be achieved, specific compositions according to whether other agents are used therewith or not, the patients age, body weight, health conditions, gender, and diet, the time and route of administration, the secretion rate of the composition, the time period of therapy, the drug(s) administered in combination or simultaneously with the specific composition, and similar factors well known in the art of medicine.

Effect of Invention

The monoacetyldiacylglycerol compounds according to the present invention inhibit the expression of IL-4 in EL-4 cells and inhibit the infiltration of inflammatory cells into bronchi in animal models. In addition, the compounds according to the present invention have an excellent effect of inhibiting the expression of CXCL-1, TNF-α or MIP-2, overcome the side effects of currently available agents for treating chronic obstructive pulmonary disease, are not toxic, and have excellent therapeutic effects. Thus, these compounds can be effectively used for the prevention, treatment and alleviation of chronic obstructive pulmonary disease.

DETAILED DESCRIPTION OF THE INVENTION

Hereinafter, the present invention will be described in further detail with reference to examples. It is to be understood, however, that these examples are for illustrative purposes and are not intended to limit the scope of the present invention.

Preparation Example 1: Preparation of Standard Cigarette Smoking (CS) Extract

Preparation Example 1-1: Experimental Materials 60 standard cigarettes CM7 (Coresta Monitoring Cigarette 7, Heinr Borgwaldt, Germany), isopropanol, ethanol (Merck, Germany), and n-heptadecane (Sigma-Aldrich, USA) were used. As a laboratory system, an automatic smoking machine (ISO 3308 standard, model: RM20, Heinr Borgwaldt) was used.

Preparation Example 1-2: Collection of Cigarette Smoke

Collection of standard cigarette CM7 (Coresta Monitoring Cigarette 7, Heinr Borgwaldt, Germany) smoke condensates was performed in a smoking room (temperature: 22±2° C.; relative humidity: 60±5%) in accordance with the ISO 3402 standard, and the cigarettes were smoked using an RM20 (Heinr Borgwaldt, Germany) automatic smoking machine (ISO 3308 standard) in accordance with the ISO 3308 standard under the following conditions: smoke volume: 35.0±0.3 ml; smoking cycle: 60±0.5 seconds; smoking time: 2.00±0.02 seconds; and tip paper length +3 mm (overwrap+3 mm). In addition, cigarette smoke condensates were collected on a 92 mm cambridge filter, ISO 3308 standard) (ISO 3308, 2000).

Preparation Example 1-3: Extraction of Cigarette Smoke Condensates

The cambridge filter having the cigarette smoke condensates collected thereon was separated in a cigarette holder and placed in each of 100 ml Erlenmeyer flasks, and 50 ml of the extraction solvent isopropanol was added thereto and well shaken. Next, the content in the flask was extracted by allowing it at room temperature for 8 hours or more. After extraction, the extract was filtered and concentrated under reduced pressure, and the concentrates in the three Erienmeyer flasks were collected in a scintillation vial and completely concentrated using nitrogen gas.

Preparation Example 1-4: Calculation of Total Particulate Matter (TPM) Content The content of TPM in the smoke mainstream was calculated using the following equation 1:

$$TPM = \frac{W_{FHA} - W_{FHB}}{N} \quad \text{Equation 1}$$

wherein
TPM: total particulate matter (mg/cig); $W_{FHA}$: the weight of the filter holder after smoking; $W_{FHB}$: the weight of the filter holder before smoking; and N: the number of cigarettes smoked per trap (cig.).

Example 1: Evaluation of Cytotoxicity of Monoacetyldlacylglycerol Compounds in EL-4 Cells EL-4 cells that are mouse T lymphoma cells were suspended in 10% fetal bovine serum-containing RPMI medium (Gibco) at a concentration of $5 \times 10^4$ cells/ml, and 100 μl of the cell suspension was seeded into each well of a 96-well plate and cultured for 12 hours. Next, the cell culture was treated with monoacetyldiacylglycerol (MADG) compounds at the concentrations shown in Table 1 below, and was then additionally cultured for 24 hours. Next, according to the instruction provided in a CCK-8 kit (Dojindo) capable of counting cells, 10 μl of CCK-8 solution was added to the kit and allowed to react for 30 minutes to 4 hours, and then the absorbance (OD) at 570 nm was measured. Cell viability was calculated using the following equation 1, and the results of the calculation are shown in Table 1 below. In equation 1, the negative control group indicates a cell culture treated with 0.2% DMSO. In Table 1 below, the following abbreviations were used: PLAG: 1-palmitoyl-2-linoleoyl-3-acetylglycerol; POAG: 1-palmitoyl-2-oleoyl-3-acetylglycerol; PSAG: 1-palmitoyl-2-stearoyl-3-acetylglycerol; PPAG: 1-palmitoyl-2-palmitoyl-3-acetylglycerol, OPAG: 1-oleoyl-2-palmitoyl-3-acetylglycerol; OSAG: 1-oleoyl-2-stearoyl-3-acetylglycerol; LPAG: 1-linoeoyl-2-palmitoyl-3-acetylglycerol; and LSAG: 1-linoeoyl-2-stearoyl-3-acetylglycerol.

Cell viability (%)=[(OD 570 nm value of MADC-treated group)/(OD 570 nm value of negative control group)]×100  Equation 1

TABLE 1

| Sample | Concentration (μg/ml) | EL-4 cell viability (%, mean ± SD) | Sample | Concentration (μg/ml) | EL-4 cell viability (%, mean ± SD) |
|---|---|---|---|---|---|
| Negative control group | 0 | 100.00 ± 0.58 | Negative control group | 0 | 100.00 ± 2.20 |
| PLAG (EC-18) | 5 | 101.94 ± 1.47 | PPAG | 5 | 106.28 ± 1.39 |
| Ec-18 | 10 | 97.54 ± 8.05 | | 10 | 105.84 ± 1.38 |
| | 20 | 91.82 ± 3.48 | | 20 | 96.59 ± 0.69 |
| | 50 | 92.67 ± 3.43 | OPAG | 5 | 98.04 ± 0.94 |
| | 100 | 95.29 ± 2.89 | | 10 | 98.91 ± 1.68 |
| | 200 | 99.74 ± 6.14 | | 20 | 99.56 ± 2.86 |
| POAG | 5 | 106.94 ± 2.69 | OSAG | 5 | 102.62 ± 2.18 |
| | 10 | 106.39 ± 1.19 | | 10 | 100.98 ± 2.37 |
| | 20 | 98.90 ± 1.16 | | 20 | 100.22 ± 0.68 |
| PSAG | 5 | 98.46 ± 0.33 | LPAG | 5 | 99.67 ± 1.15 |
| | 10 | 100.66 ± 1.25 | | 10 | 98.91 ± 0.50 |
| | 20 | 103.30 ± 2.15 | | 20 | 99.13 ± 1.18 |
| | | | LSAG | 5 | 103.82 ± 1.80 |
| | | | | 10 | 101.85 ± 1.00 |
| | | | | 20 | 98.15 ± 1.82 |

As shown in Table 1 above, the cell viabilities of EL-4 cells at varying concentrations of the monoacetyldiacylglycerol (MADG) compounds were analyzed, and as a result, it was shown that EC-18 showed no cytotoxicity at a concentration of 200 µg/mL or less, and the other compounds showed no cytotoxicity at a concentration of 20 µg/mL or less.

Example 2: Inhibition of EL-4 mRNA Expression by Monoacetyldacylglycerol Compounds Based on the results of Example 1, each of the monoacetyldiacylglycerol compounds was added to EL-4 cells at a concentration of 20 µg/mL, and the effect thereof on the inhibition of PMA-induced expression of IL-4 mRNA in the EL-4 cells was measured. Specifically, the expression level of IL-4 mRNA induced by PMA (1 ng/mL) was measured using real-time polymerase chain reaction (real-time PCR) and quantitative real time polymerase chain reaction (qPCR). For cell preparation, EL-4 cells were seeded into a 6-well plate at a concentration of $1 \times 10^6$ cells/well and cultured for 12 hours, after which the cells were treated with each of the monoacetyldiacylglycerol compounds at a concentration of 20 µg/mL for 1 hour and treated with PMA at a concentration of 1 ng/m, followed by culture for 12 hours. Total RNA was extracted from the cells using Trizol B (Invitrogen, USA) and quantified, and then cDNA was synthesized from the total RNA using an Omniscript RT kit (Qiagen, GmbH, Hilden, Germany). The synthesized cDNA as a template was mixed with each of the IL-4 and GAPDH primers shown in Table 2 below and was subjected to PCR using a PCR mix (PCR Master Mix, Bioneer, Korea) under the following conditions: denaturation at 94° C. for 5 minutes; and then 30 cycles, each consisting of 30 sec at 95° C., 45 sec at 60° C., and 45 sec at 72° C.; followed by enzyme inactivation at 72° C. for 10 minutes. The results of measuring the percent inhibition of expression of IL-4 mRNA in EL-4 cells as described above are shown in Table 3 below. The designation of each of the samples shown in Table 3 below is as described with respect to Table above.

TABLE 2

| Genes | Primers | |
|---|---|---|
| 1F-4 | Sense | 5'- GAA TGT ACC AGG AGC CAT ATC -3' |
| | Antisense | 5'- CTC AGT ACT ACG AGT AAT CCA -3' |
| GAPDH | Sense | 5'- AAC TTT GGC ATT GTG GAA GG -3' |
| | Antisense | 5'- ACA CAT TGG GGG TAG GAA CA -3' |

TABLE 3

| Sample | Concentration (µg/mL) | PMA (1 ng/mL) | Expression level of IL-4 mRNA (percentage relative to PMA-treated group) | Inhibition (%) |
|---|---|---|---|---|
| Negative control group | 0 | − | 72.13 ± 7.13 | — |
| PMA-treated group | 0 | + | 100.01 ± 5.91 | — |
| PLAG | 20 | + | 78.17 ± 6.26 | 21.83 |
| POAG | 20 | + | 75.47 ± 13.15 | 24.53 |
| PSAG | 20 | + | 70.49 ± 17.78 | 29.51 |
| PPAG | 20 | + | 48.62 ± 19.38 | 51.38 |
| OPAG | 20 | + | 58.58 ± 21.74 | 41.42 |
| OSAG | 20 | + | 55.84 ± 25.77 | 44.16 |
| LPAG | 20 | + | 61.11 ± 27.49 | 38.89 |
| LSAG | 20 | + | 41.62 ± 17.61 | 58.38 |

As shown in Table 3 above, the expression level of IL-4 in the PMA-treated group increased, and the monoacetyldiacylglycerol compounds inhibited the expression IL-4 by 20-50% compared to that in the PMA-treated group (100%).

Example 3: Chronic Obstructive Pulmonary Disease Models and Sample Administration To make COPD mouse models, 8-week-old male BALB/c mice were anesthetized with 7% chloral hydrate, and then intratracheally inhaled with 100 µl of a 1:1 mixture of 100 µg/ml of LPS and 4 mg/ml, of standard cigarette smoking (CS) extract (LPS+CS mixture) once a week for 3 weeks. Specifically, when the mice were inactive after slight anesthesia, 100 µl of the LPS+CS mixture was intratracheally inhaled into the nose (50 µl) and the mouth (50 µl) in a state in which the front teeth of the mice were fixed with rubber bands. EC-18 was dissolved in 0.5% CMC (carboxymethyl-cellulose sodium) to concentrations of 30 mg/kg and 60 mg/kg, and administered orally to the mice at 1 hour before intratracheal inhalation of 100 µl of the PS+CS mixture. The mice were divided into: (i) an untreated normal group (intact); (ii) a control group treated with LPS+CS (COPD-control); (iii) a test group administered orally with 30 mg/kg of EC-18 at 1 hour before treatment with LPS+CS; and (iv) a test group administered orally with 60 mg/kg of EC-18 at 1 hour before treatment with the LPS+CS mixture. After completion of the experiment, blood, bronchoalveolar lavage fluid and lung tissue were isolated from the mice of each of the groups.

Example 4: Isolation of Bronchoalveolar Lavage Fluid (BALF) and Counting of Total Cells After blood collection, the mice were dissected. To isolate cells from the bronchoalveolar lavage fluid (BALF), a syringe containing 1 ml of FBS-free DMEM medium was injected into the trachea and fixed with a string, and then cells were separated by performing circulation three times and were treated with ACK solution at 37° C. for 5 minutes to lyse red blood cells. Next, the cells were washed with FBS-free DMEM medium and then stained with 0.04% trypan blue, after which the number of total cells was measured. The results of the measurement are shown in Table 4 below.

TABLE 4

| | Inflammatory cell count | | | |
|---|---|---|---|---|
| Group | Total cell ($10^6$) | % inhibition | Neutrophil | % inhibition |
| NC | 20.1 ± 4.41 | — | 0.5 ± 0.12 | — |
| COPD | 95.4 ± 16.99[#] | — | 202.8 ± 24.48[#] | — |
| EC18-30 | 81.0 ± 12.14 | 15.1 | 196.9 ± 31.61 | 3 |
| EC18-60 | 52.8 ± 10.41* | 44.8 | 116.8 ± 37.43* | 42 |

As a result, as shown in Table 4 above, lung inflammation is the important feature of chronic obstructive pulmonary disease (COPD), and an increase in the number of neutrophils among inflammatory cells was observed. In the case of the COPD-induced group, an increase in the number of inflammatory cells in the bronchoalveolar lavage fluid compared to that in the normal control group was observed, and the number of neutrophils among inflammatory cells significantly increased. However, in the case of the drug-administered group administered with 30 mg/kg of EC-18, the number of total inflammatory cells was inhibited by 15.1%, and no great change in the number of neutrophils was observed. In the case of the group administered with 60 mg/kg of EC-18, the number of total inflammatory cells was inhibited by 44.8% (P<0.05), and the number of neutrophils was also inhibited by 42% (P<0.05).

Example 5: Measurement of Numbers of CD4+ Cells and Neutrophils (Gr-1+ Cells) by Flow Cytometry The separated BAL cells were adjusted to $5 \times 10^5$ cells, and then subjected to immunofluorescence staining at 4° C. PE-anti-CD4 (553047, BD Pharmingen) and PE-anti-Gr-1 (553128, BD Pharmingen) were added to the cells which were then incubated on ice for 30 minutes. After incubation, the cells were washed three times or more with phosphate buffered saline, and then the frequency of $CD4^+$ cells and $Gr-1^+$ neutrophils was analyzed using the Cell Quest program (643274, BD Biosciences) of a flow cytometer. Next, based on total cells, the absolute number of cells in each tissue was calculated.

TABLE 5

| | Cell count | | | |
|---|---|---|---|---|
| Group | $CD4^+$ cells $(10^4)$ | % inhibition | $Gr-1^+$ neutrophils $(10^4)$ | % inhibition |
| NC | 7.5 ± 1.49 | — | 0.4 ± 0.08 | — |
| COPD | 510.1 ± 157.65 | — | 33.9 ± 8.19 | — |
| EC18-30 | 308.2 ± 66.78 | 39.6 | 20.0 ± 6.97 | 40.9 |
| EC18-60 | 152.8 ± 66.25 | 70.0 | 12.6 ± 4.93 | 62.7 |

As a result, as shown in Table 5 above, the numbers of $CD4^+$ cells and $Gr-1^+$ neutrophils in the COPD-induced group all greatly increased compared to those in the normal control group. However, in the group administered with 30 mg/kg of EC-18, the number of $CD4^+$ cells was inhibited by 39.6% and the number of $Gr-1^+$ neutrophils was inhibited by 40.9% (P<0.05), compared to those in the COPD-induced group. In addition, in the group administered with 60 mg/kg of EC-18, the number of $CD4^+$ cells was inhibited by 70.0%, and the number of $Gr-1^+$ neutrophils was inhibited by 62.7% (P<0.05).

Example 6: Measurement of Expression Levels of CXCL-1. TNF-α and MIP-2 in Bronchoalveolar Lavage Fluid by ELISA The levels of CXCL-1, TNF-α and MIP-2 in the bronchoalveolar lavage isolated from the mice were measured by an enzyme-linked immunosorbent assay (ELISA). An antibody specific for each of CXCL-1, TNF-α and MIP-2 was diluted in coating buffer (291195, R&D System), coated on microwells, and then incubated overnight at 4° C. Each well was washed three times with washing buffer, and then 100 μl of serum (10-fold diluted) was added to each well. Each well was allowed to stand at room temperature for 1 hour, and then washed twice with washing buffer antibody, after which each well was treated with 100 μl of avidin-conjugated HRP (DY998, R&D System) and allowed to stand at room temperature for 1 hour, followed by washing. 100 μl of a TMB substrate was added to each well which was then allowed to stand in a dark room for 30 minutes and treated with 50 μl of a stop solution. Next, the absorbance at 450 nm was measured using an ELISA reader (Emax, Molecular Devices), and the percent inhibition of expression was calculated. The results of the calculation are shown in Table 6 below.

TABLE 6

| Group | CXCL-1 (pg/mL) | % inhibition |
|---|---|---|
| NC | 71.9 ± 15.93 | — |
| COPD | 312.6 ± 63.16 | — |
| EC18-30 | 264.3 ± 79.77 | 15.4 |
| EC18-60 | 142.9 ± 26.99 | 54.3 |

As shown in Table 6 above, the production of CXCL-1 in the bronchoalveolar lavage fluid in the COPD-induced group significantly increased compared to that in the normal control group. However, the production of CXCL-1 in the group administered with 30 mg/kg of EC-18 was inhibited by 15.4% compared to that in the COPD-induced group, and the production of CXCL-1 in the group administered with 60 mg/kg of EC-18 was inhibited by 54.3% (P<0.01) compared to that in the COPD-induced group.

TABLE 7

| Group | TNF-α(pg/mL) | % inhibition |
|---|---|---|
| NC | 1.5 ± 0.34 | — |
| COPD | 35.0 ± 9.68 | — |
| EC18-30 | 22.4 ± 13.98 | 36.0 |
| EC18-60 | 13.4 ± 5.33 | 61.8 |

In addition, as shown in Table 7 above, the production of TNF-α in the bronchoalveolar lavage fluid in the COPD-induced group significantly increased compared to that in the normal control group. However, the production of TNF-α in the group administered with 30 mg/kg of EC-18 was inhibited by 36.0% compared to that in the COPD-induced group, and the production of TNF-α in the group administered with 60 mg/kg of EC-18 was inhibited by 61.8% (P<0.05) compared to that in the COPD-induced group.

TABLE 8

| Group | MIP-2 (pg/mL) | % inhibition |
|---|---|---|
| NC | 12.0 ± 1.75 | — |
| COPD | 48.7 ± 15.02 | — |
| EC18-30 | 28.9 ± 5.72 | 40.6 |
| EC18-60 | 17.6 ± 4.07 | 63.8 |

In addition, as shown in Table 8 above, the production of MIP-2 in the bronchoalveolar lavage fluid in the COPD-induced group significantly increased compared to that in the normal control group. However, the production of MIP-2 in the group administered with 30 mg/kg of EC-18 was inhibited by 40.6% compared to that in the COPD-induced group, and the production of MIP-2 in the group administered with 60 mg/kg of EC-18 was inhibited by 63.8% (P<0.05) compared to that in the COPD-induced group.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention should be defined by the appended claims rather than the detailed description, and it should be understood that all modifications or variations derived from the meanings and scope of the present invention and equivalents thereof are included in the scope of the present invention.

The invention claimed is:

1. A method of treating a chronic obstructive pulmonary disease in a patient, comprising administering to a patient in need of such treatment a pharmaceutically acceptable composition comprising an effective amount of a purified compound of Formula 2:

[Formula 2]

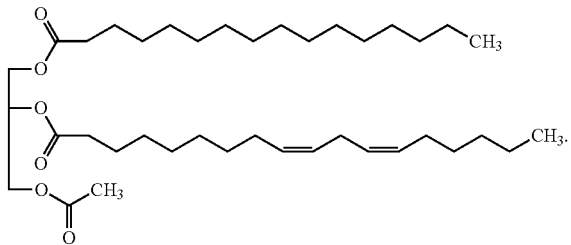

2. The method according to claim 1, wherein the chronic obstructive pulmonary disease is chronic bronchitis.

3. The method according to claim 1, wherein the monoacetyldiacylglycerol compound reduces the secretion of one or more protein selected from a group consisting of IL-4, CXCL-1, TNF-.alpha. and MIP-2 levels.

4. The method according to claim 1, wherein the monoacetyldiacylglycerol compound reduces the number of inflammatory cells around the bronchi or vessels or the numbers of $CD4^+$ cells and $Gr-1^+$ neutrophils.

5. The method according to claim 1, wherein the chronic obstructive pulmonary disease is emphysema.

* * * * *